(12) United States Patent
Wilkinson et al.

(10) Patent No.: US 6,409,971 B1
(45) Date of Patent: Jun. 25, 2002

(54) DEVICE AND METHOD FOR COLLECTING AND TRANSFERRING A URINE SPECIMEN

(75) Inventors: Bradley M. Wilkinson, North Haledon; Robert S. Golabek, Jr., Towaco, both of NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/369,728

(22) Filed: Aug. 6, 1999

(51) Int. Cl.[7] .............................. B01L 3/00; A61B 5/00
(52) U.S. Cl. .......................... 422/103; 422/61; 422/99; 422/102; 422/104; 600/573; 600/574; 600/576; 600/577; 604/317; 604/323; 604/326; 604/327; 604/328; 604/329
(58) Field of Search ................................ 422/102–104, 422/99, 58, 61; 604/317, 326–329, 323; 600/573–577, 579; 435/288.1, 304.1

(56) References Cited

U.S. PATENT DOCUMENTS

| | | | |
|---|---|---|---|
| 3,485,233 A | * 12/1969 | Cord | 128/2 |
| 3,750,647 A | 8/1973 | Gleason et al. | 128/2 F |
| 4,106,490 A | 8/1978 | Spilman et al. | 128/2 F |
| 4,116,066 A | 9/1978 | Mehl et al. | 73/421 R |
| 4,121,306 A | 10/1978 | Beringman et al. | 4/144.2 |
| 4,252,132 A | * 2/1981 | Kuntz | 128/761 |
| 4,258,032 A | 3/1981 | Mehl | 424/148 |
| 4,300,404 A | 11/1981 | Mehl et al. | 73/863.52 |
| 4,335,730 A | 6/1982 | Grffin | 128/761 |
| 4,393,881 A | 7/1983 | Shah | 128/760 |
| 4,492,258 A | 1/1985 | Lichtenstein et al. | 141/1 |
| 4,557,274 A | * 12/1985 | Cawood | 128/760 |
| 4,761,379 A | 8/1988 | Williams et al. | 435/296 |
| 4,769,215 A | 9/1988 | Ehrenkranz | 422/58 |
| 4,895,167 A | 1/1990 | Guala | 128/760 |
| 5,069,878 A | 12/1991 | Ehrenkranz | 422/61 |
| 5,147,342 A | 9/1992 | Kane et al. | 604/356 |
| 5,251,639 A | 10/1993 | Rentsch | 128/761 |
| 5,255,689 A | * 10/1993 | Kenda | 128/762 |
| 5,422,076 A | 6/1995 | Jones | 422/102 |
| 5,457,823 A | * 10/1995 | Mojena | 4/144.2 |
| 5,569,225 A | 10/1996 | Fleury | 604/223 |
| 5,797,855 A | 8/1998 | Hazard et al. | 600/513 |
| 5,849,505 A | 12/1998 | Guirguis | 435/7.2 |
| 5,871,476 A | * 2/1999 | Hand | 604/317 |
| 5,893,176 A | 4/1999 | Magiera et al. | 4/144.4 |
| 5,894,607 A | 4/1999 | Van Den Burg | 4/144.2 |
| 5,894,608 A | 4/1999 | Birbara | 4/144.3 |
| 5,897,840 A | 4/1999 | Owens, Jr. et al. | 422/102 |
| 6,171,261 B1 | * 1/2001 | Niermann et al. | 600/573 |
| 6,235,010 B1 | * 5/2001 | Wilkinson et al. | 604/356 |

* cited by examiner

Primary Examiner—Jeffrey Snay
Assistant Examiner—Kathryn Bex
(74) Attorney, Agent, or Firm—Nanette S. Thomas (57) ABSTRACT

The urine collection device of the present invention is an open collection system designed to collect and transfer a liquid urine specimen into a non-evacuated tube through a valve. The device is designed to be user friendly and has a finger placement platform so that one can hold the container without risk of contaminating the inside of the container or becoming exposed to the specimen. The specimen is transferred into the non-evacuated tube when the tube is connected to the valve port. A blunt cannula is used on the collection tube to transfer the specimen thereby avoiding exposure to sharps. The collection tube is attached to the urine collection device at an oblique angle. Gravity allows the specimen to be transferred into the tube and automatically stop at a pre-determined volume based on the oblique angle. The urine collection device with the tube attached may be placed on a flat surface without tipping over. When the filled collection tube is removed from the urine collection device, another tube may be attached for further filling. The self-sealing feature of the valve prevents the remaining liquid from leaking out. The filled collection tube may then be shipped to a laboratory for further analysis.

6 Claims, 5 Drawing Sheets

DEVICE AND METHOD FOR COLLECTING AND TRANSFERRING A URINE SPECIMEN

BACKGROUND OF THE INVENTION

1. Field of the Invention.

The present invention relates generally to a device and a method for collecting and transferring biological fluids. More particularly, the present invention relates to a device and a method for collecting and transferring a urine specimen in conjunction with a collection tube.

2. Description of Prior Art.

Biological fluids are collected periodically for laboratory analysis. Laboratory equipment that performs the analysis may only accept biological fluids stored in a test tube. However, a conventional test tube may be too small for the convenient collection of many biological fluids, such as urine. As a result, specimens often are collected in a fairly large container with a widely open top. After collection of the fluid in the container, the container is delivered to a medical technician. The technician then transfers a portion of the fluid to a test tube that can be sealed and transported to a laboratory for analysis. The transfer of biological fluid from the collection container to the test tube is an unpleasant task that creates the risk of contaminating the specimen or exposing the medical technician to potentially harmful pathogens in the specimen.

Some biological fluids, such as blood, are collected from patients with assemblies that include a vacuum tube and a double-ended needle cannula. One end of the needle cannula is placed in communication with the biological fluid, typically by piercing the skin of a patient. The opposite end of the needle cannula is urged through a vacuum seal into the vacuum tube. Low pressure within the vacuum tube generates a flow of the bodily fluid through the needle cannula and into the tube. Such vacuum tubes are very convenient and efficient for collecting blood samples. However, for urine specimen collection, vacuum tubes are not very useful because vacuum tubes only have a limited shelf life due to a gradual migration of gas molecules through the walls of the tube. Additionally, sharps or pointed cannula require careful shielding to avoid potential skin punctures.

In urine collection, some collection containers have a test tube that is attached. In these devices, a portion of the urine specimen in the container is automatically transferred to the test tube. The test tube then may be separated from the container, sealed and shipped to a laboratory for analysis. However, these prior art assemblies can lead to leakage during the initial collection of the specimen or after the separation of the test tube from the collection container. Additionally, control of the volume of the specimen in the test tube may vary from sample to sample. An improvement for controlling the volume in each specimen sample taken is needed to assure accurate results in the subsequent laboratory analysis. Also, the use of a non-sharp or blunt cannula in the transfer of the specimen from the collection container to the test tube is desired to avoid potential skin puncturing of the medical technician. Also, a collection container designed to avoid contact with the user to prevent contamination of the specimen would offer significant advantages. Prior art assemblies of collection containers can come into contact with the user's hands during collection which contaminate the specimen in the collection container. Finally, there is a need for a collection container to use a non-evacuated vacuum tube to avoid the potential limited shelf life of the vacuum tube.

SUMMARY OF THE INVENTION

The invention is directed to a urine collection device for use with a collection tube. Included in the urine collection device is an arcuate base, an open top defining a plane, and a plurality of opposing side walls extending from the base to the open top. The base has a top surface, a bottom surface and a conduit passing therethrough. Inclined is the top surface with respect to the plane. The conduit is located at the lowest gravitational point on the top surface. Further included in the urine collection device is an integrated valve in fluid communication with the conduit and the base. The valve is recessed within the base. The valve is also fixably and angularly attached to the arcuate base such that when the collection tube is attached to the valve, the collection tube is obliquely positioned with respect to the plane for collecting a predetermined volume in the collection tube.

The urine collection device preferably further comprises a tube holder fin centrally located on the bottom surface for holding the collection tube during collection. A plurality of releasable snap-fit arms may be disposed on the top surface of the collection device for holding the collection tube during storage of the device. The snap-fit arms are positioned on the top surface to assist in channeling the specimen toward the conduit.

A method for collecting and transferring a urine specimen comprises the steps of holding a urine collection device of the type having an arcuate base with an inclined top surface. The top surface leads to a near a low gravitational point on the top surface. A valve angularly attached and recessed in the base is also included in the device. The valve is in fluid communication with the conduit and the base. The next step is holding the urine collection device by a finger placement platform horizontally positioned on the device. The specimen is then collected in the urine collection device is the next step in this process. Next, a collection tube is attached to the device at an oblique angle for filling the collection tube to a predetermined volume. Finally, the collection tube is removed from the device for shipment to a laboratory for analysis.

BRIEF DESCRIPTION OF THE DRAWINGS

A preferred embodiment of the invention is now described in, greater detail by way of reference to the following drawings, wherein.

DETAILED DESCRIPTION OF THE INVENTION

Turning now to the drawings, wherein like numerals denote like components, FIGS. 1–8 depict one embodiment of a urine collection device assembly 10. Urine collection device assembly 10 comprises a urine collection device 16 and a collection tube 12 removably attached to urine collection device 16. A specimen collection can be taken either with collection tube 12 attached or not attached to the collection device. Attachment of the collection tube allows the transfer of the specimen from the device to the collection tube for shipment to a laboratory for analysis. If collection tube 12 is attached, immediate transfer of the specimen in urine collection device 16 proceeds into collection tube 12. Collection tube 12 can then be removed and another tube can be attached if more samples are desired. The advantage of collecting the specimen without tube 12 attached is that the medical technician has control over the transfer of the specimen. This control is especially important if the patient attempts to tamper with tube 12 during collection.

Urine collection device 16 includes an arcuate base 14, an open top 20 which defines a plane "A," and a side wall 24 extending from base 14 to open top 20. Arcuate base 14 further includes a top surface 30, a bottom surface 32, and a conduit 34 passing through top surface 30 and bottom surface 32. Preferably, top surface 30 is inclined with respect to plane "A." Bottom surface 32 may be inclined as well, but it does not have to be inclined for device 16 and assembly 10 to function. However, the purpose of base 14 being arcuate or curved is to impart this incline on top surface 30 and allow the specimen to flow toward conduit 34.

Figure 6:
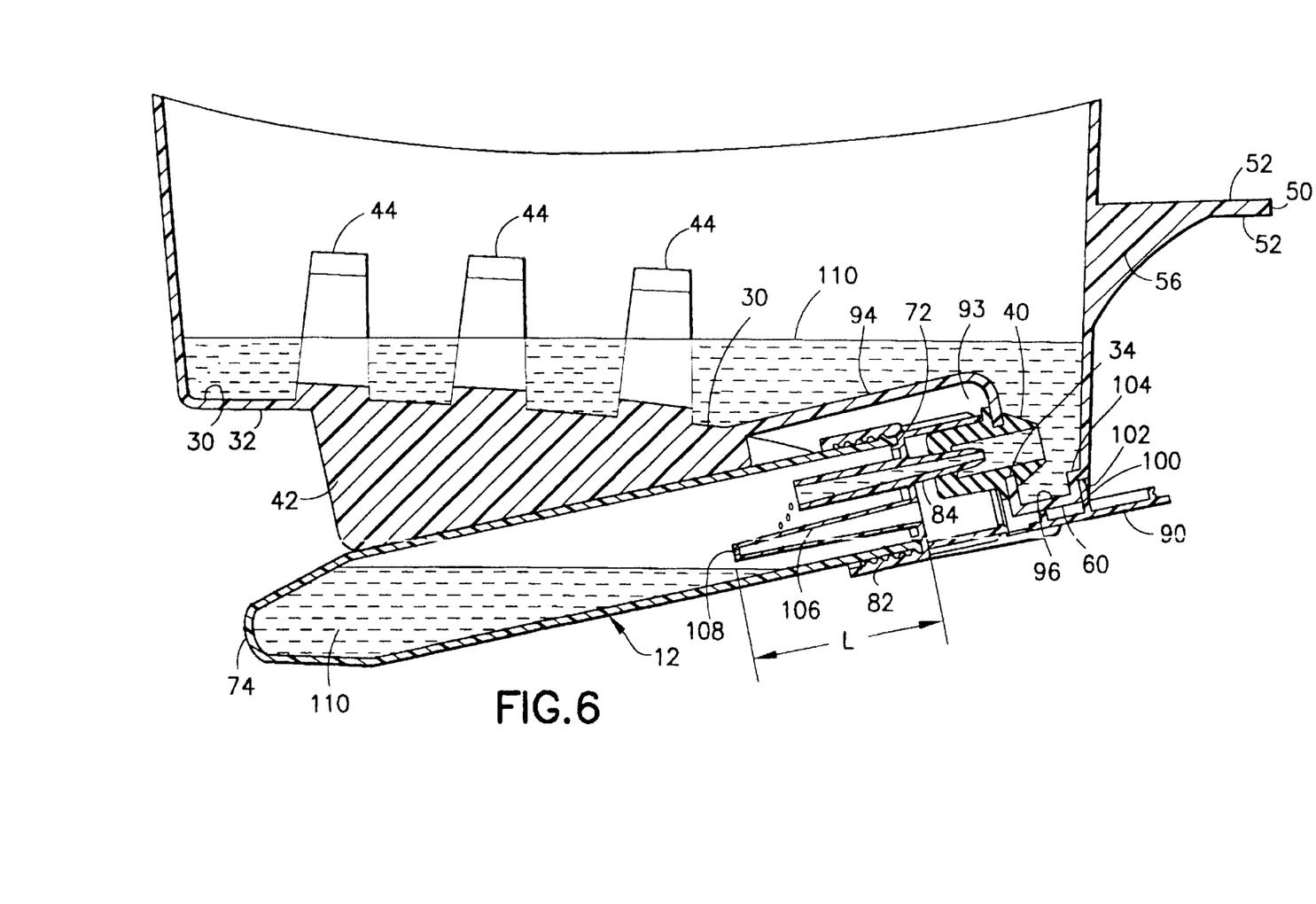
FIG. 6 is a cross-sectional view taken along line 6—6 of FIG. 4.

As shown in FIG. 6, conduit 34 is preferably located on base 14 at a region 96 which is the lowest gravitational area on top surface 30. The purpose for region 96 is to allow the specimen in urine collection device 16 to flow by gravity down top surface 30 and toward conduit 34.

Collection device 16 further includes valve 40 attached to base 14 through conduit 34. Attachment of valve 40 into conduit 34 allows fluid communication among valve 40, conduit 34 and base 14. As the specimen flows toward conduit 34, it also flows to valve 40.

Figure 7:
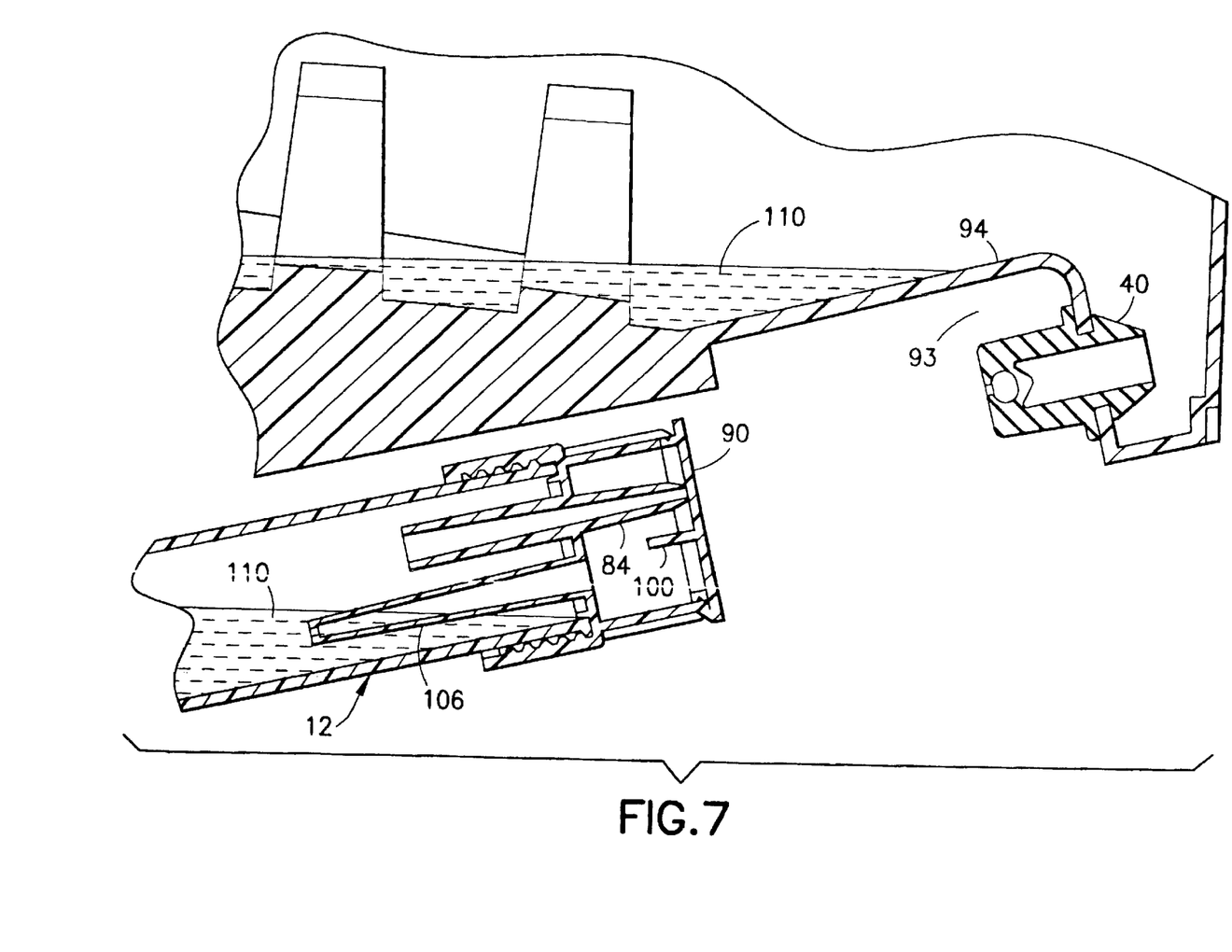
FIG. 7 is an enlarged and exploded view of FIG. 6 unassembled.
Figure 8:
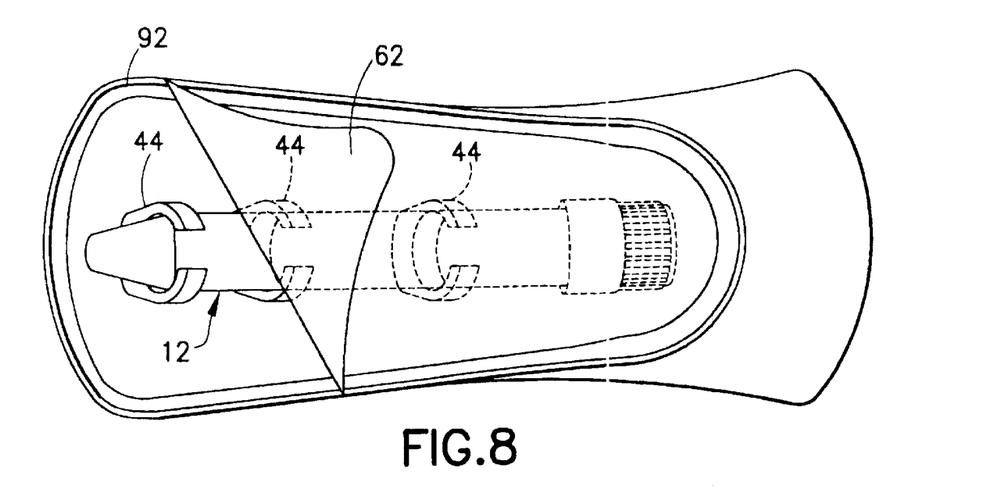
FIG. 8 is a top view illustrating placement of a lid on the urine collection device with the collection tube stored in the device.

Valve 40 as shown in FIG. 7, is a closed valve and does not open until a piercing member 84 on collection tube 12 pierces it. Valve 40 self-seals after piercing member 84 is removed so no further specimen flows out of valve 40. Valve 40 is preferably recessed in base 14 in a recess area 93. Recessed area 93 has a top area 94 on top surface 30 as shown in FIG. 6.

Top area 94 is inclined in the opposite direction of top surface 30. This configuration allows the device to be tilted with respect to a flat surface in order to stop the flow of the specimen toward the valve. After the tube is filled to a predetermined volume, tilting the device in an orientation parallel to the tube and away from valve 40 assures the specimen will not flow toward the valve. This stoppage of flow is due to the incline of top area 94 which is in opposite orientation to top surface 30. Once the tube is removed in this tilted position, valve 40 closes and the device can be set back on the flat surface. Recessing valve 40 provides for protection from any potential exposure to the specimen due to splatter when valve 40 is pierced or when piercing member 84 is removed.

Figure 3:
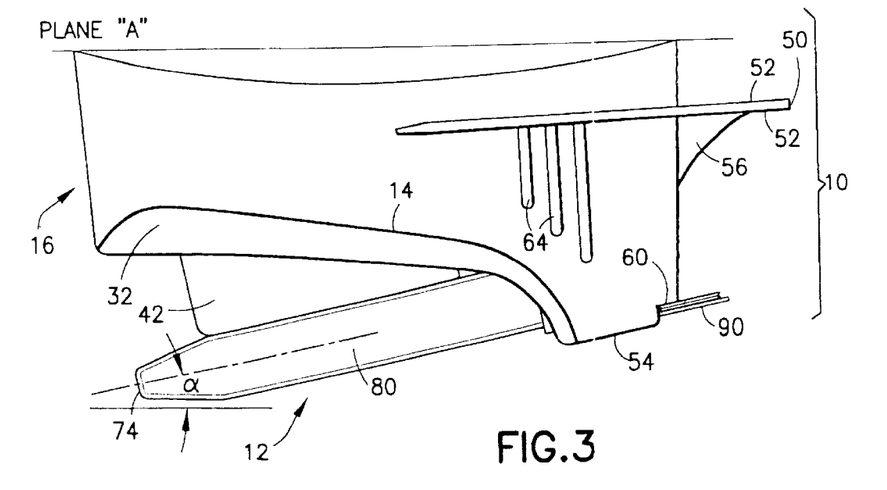
FIG. 3 shows an assembled side view of the urine collection device in FIG. 1.

Furthermore, valve 40 is preferably fixably and angularly attached to base 14. As shown in FIG. 3, when collection tube 12 is attached to urine collection device 16, urine collection device assembly 10 is formed and collection tube 12 is obliquely positioned with respect to plane "A." Upon attachment of piercing member 84 through valve 40, collection tube 12 is in fluid communication with valve 40, base 14, and urine collection device 16. This position tilts collection tube 12 at an angle "α" with respect to plane "A." Angle "α" is defined as the angle formed from the centerline of collection tube 12 to a line substantially parallel to plane "A." Angle "α" is directly dependent and equivalent to the position of valve 40 with respect to plane "A." It is the angularity of valve 40 and hence angle "α" that determines the volume of specimen that is transferred from the collection device into collection tube 12. By changing angle "α," the volume in collection tube 12 can be varied. Thus, a predetermined volume in collection tube 12 can be calculated or calibrated by changing angle "α" to provide for the desired volume to be transferred. Thus, the oblique position of attached collection tube 12 is characterized by an angle "α" shown in FIG. 3

In addition, an alternate volume control for the transfer of the specimen is an air flow tube 106 as shown in FIG. 6. The air flow tube has a length "L" and a channel 108 that allows the flow of air to escape from the collection tube as the specimen flows into the collection tube. Once the specimen reaches a level where the channel is blocked, the flow of specimen from the device to the collection tube stops. Thus, in addition to varying angle "α", the length of the air flow tube can be altered to control the desired volume of the specimen to be transferred.

Attachment of valve 40 into conduit 34 on base 14 is preferably done by a permanent snap fit design. It is well known to those skilled in the art the various snap fit designs valve 40 and mating conduit 34 may include. Such snap fit designs include cantilever snaps, annular snap joints and discontinuous annular snap joints. In addition, valve 40 may be attached by other methods of assembly known by those skilled in the art. Such methods include ultrasonic welding, heat welding, adhesive bonding, multi-shot molding and in-mold assembly. Valve 40, alternatively, may be integrally formed on base 14. Thus, valve 40 and base 14 may be made of the same material and molded together at the same time. Such materials would include ethylene-propylene-dienemonomer, styrene-butadiene block co-polymers, polyisoprene, polyisobutylene, silicone based rubber, polyester based polyurethane, and polybutadiene elastomers. Preferably, valve 40 is a separate component that is attached to base 14. This feature allows base 14 to be made of a more rigid material than valve 40. A rigid material is preferred for base 14 because it may provide more structural integrity than having the collection device being made entirely out of an elastomeric material with valve 40.

Figure 1:
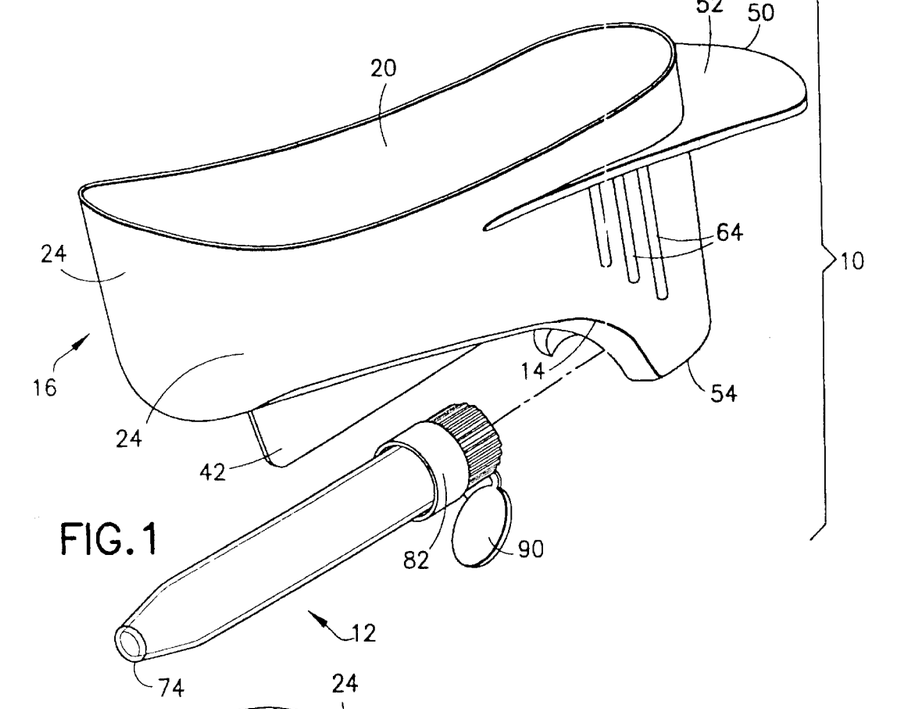
FIG. 1 is an exploded top perspective view of the urine collection device of the present invention in conjunction with a collection tube.
Figure 2:
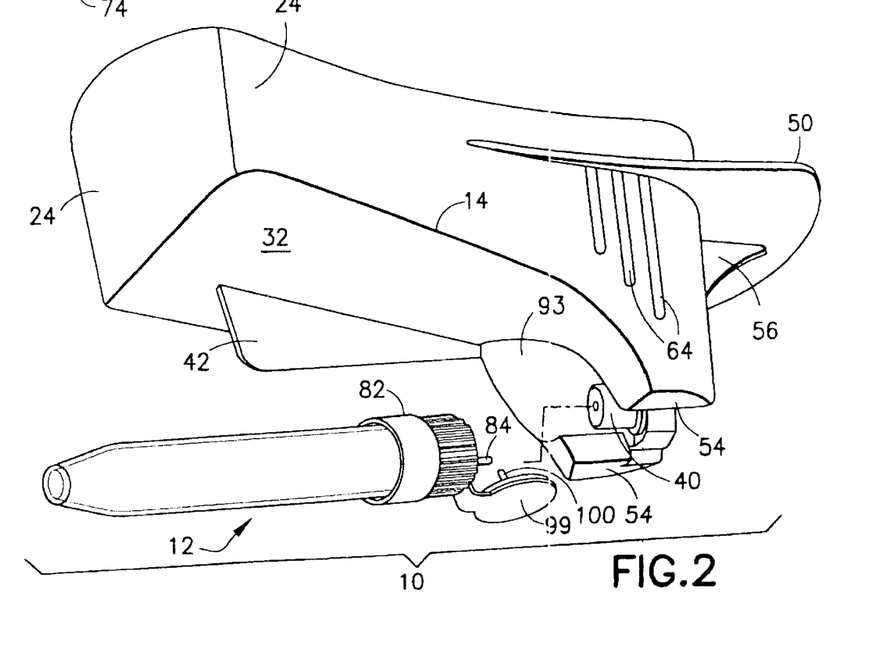
FIG. 2 shows an exploded bottom perspective view of the urine collection device of the present invention.

Urine collection device 16 further includes a tube fin holder 42 centrally located on bottom surface 32 for holding collection tube 12 during collection. Preferably, tube fin holder 42 is a single fin as shown in FIG. 1 and FIG. 2. However, tube fin holder 42 could be composed of a plurality of fins disposed on bottom surface 32. The advantage of having a single fin is for ease of attaching and removing collection tube 12. Tube fin holder 42 provides stability to collection tube 12. The central location of tube fin holder 42 on bottom surface 32 provides stability of collection tube 12 when it is attached to urine collection device 16. If the plurality of fins are used, all the fins may be centrally located in order to maintain stability of the test tube. If the fins are not centrally located a balance among the fins must exist to maintain stability.

Urine collection device 16 further includes a plurality of snap fit arms 44 disposed and positioned on top surface 30. Snap fit arms 44 are for providing a secure holding place for collection tube 12 during storage of urine collection device 16. The collection tube releasably snap fits in the snap-fit arms.

A finger placement platform 50 is also included on urine collection device 16. Finger placement platform 50 is preferably perpendicularly and horizontally mounted to side wall 24, although other orientations may be employed. Preferably only one platform 50 is mounted to the side wall. However, more than one could be attached to the side wall. The purpose of platform 50 is to provide the user and medical technician a means for holding the urine collection device without risking contamination of the inside of the device. Contamination of the specimen could affect the results of the subsequent laboratory analysis. In addition, the platform reduces the risk of getting the specimen on the user's or medical technician's hands.

Platform 50 has gripping surfaces 52 disposed on the top and bottom of the platform as shown in FIG. 3 and FIG. 6. Gripping surface 52 is preferably perpendicularly and horizontally oriented from the side wall. Gripping surfaces 52 assist in holding device 16 giving slip resistant holding to the device. Preferably, the gripping surfaces are on the top and bottom of the platform to provide maximum gripping surface area. However, it is within the scope of the invention to provide a gripping surface on only one side of the platform.

Gripping surfaces 52 can be made in many different forms as known by those skilled in the art. These forms include contours, ridges, ribs or bumps molded in platform 50. Gripping surfaces 52 may also have an abrasive form such as having a slight abrasive surfacing on the platform with a grain size between about 100 to about 220. In addition, the gripping surfaces may have the form of a multi-material overlaying such as having a softer elastomeric material surrounding the harder plastic of the platform.

Platform 50 may include a support rib 56 preferably centrally and perpendicularly attached to the bottom of platform 50 and also mounted to side wall 24, although other orientations may be employed. The function of support rib 56 is to give added strength to platform 50. In addition, the support rib acts as an additional holding platform to hold device 16.

A planar portion 54 is further included in arcuate base 14 of the urine collection device. Preferably, planar portion 54 is located adjacent to integrated valve 40 as shown in FIG. 2. The function of portion 54 is to provide flat surface support to urine collection device 16. Planar portion 54 works by providing a flat surface so the device can rest securely on a corresponding flat surface. This support is available with or without collection tube 12 attached to device 16. Preferably, finger placement platform 50 is on the same side of device 16 as planar portion 54. This orientation provides for better ease of use of device 16. More than one planar portion may be incorporated into the device for added flat surface supports.

Figure 4:
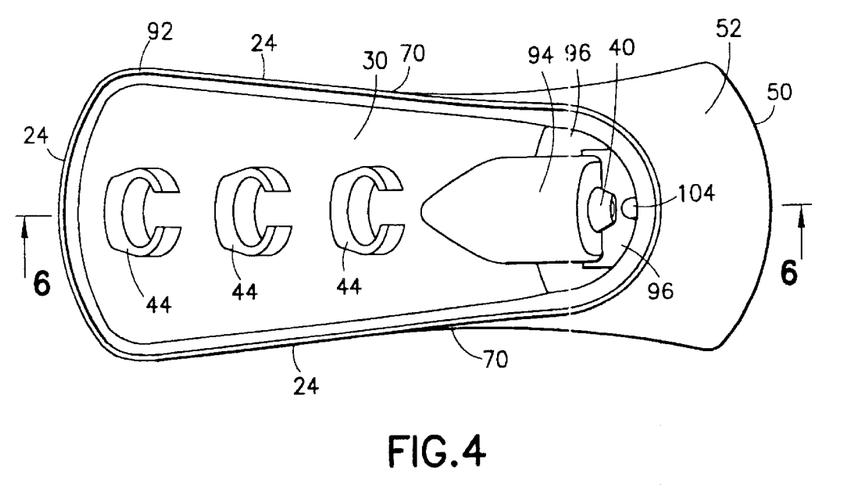
FIG. 4 illustrates a top view of the urine collection device of FIG. 1.

Planar portion 54 also has a locking platform 60 located beneath finger placement platform 50. As shown FIG. 5, locking platform 60 has a retaining depression 102 on the outside of the device. FIG. 4 illustrates a top portion 104 located on the inside of device 16. The function of locking platform 60 is to provide for secure and releasable locking of collection tube 12 to device 16 during sample collection. Locking platform 60 functions by holding the edges of a closure 90 on tube 12 as shown in FIG. 4. Closure 90 releasably snaps into locking platform 60 to provide releasable and secure locking to tube 12. A retaining plug 100 on closure 90 inserts into mating component retaining depression 102 for releasable and secure locking of tube 12. Preferably, retaining plug 100 and retaining depression 102 are mating and releasable snap fits.

A plurality of ribs 64 vertically oriented on the side wall is also included in the urine collection device. Ribs 64 assists in securely holding device 16 by allowing the user or medical technician to hold device 16 by side wall 24. If the ribs are used in addition to the finger platform additional securement of the device is possible.

Side wall 24 further may have an oblong shape as shown in FIG. 2, FIG. 4 and FIG. 7. The shape includes a plurality of depressions 70. This shape allows the user or medical technician to hold the device in the middle for transport to a flat surface. However, it is preferred that finger placement platform 50 be used for holding device 16 to avoid contamination of the inside of device 16 and avoid exposure to the specimen.

Open top 20 is further characterized by having a rim 92 on the top of the side wall as shown in FIG. 7. A lid 62 is attached to rim 92 when urine collection device 16 is in storage. Such attachment methods known to one skilled in the art include heat sealing, adhesive bonding, and snap fitting. The function of lid 62 is to maintain the integrity and sterility of the inside of urine collection container 16. Lid 62 is removed prior to use.

Collection tube 12 of urine collection device assembly 10 further includes a top 72, a closed bottom 74 and cylindrical side walls 80 extending from closed bottom 74 to top 72. A cap is disposed on top 72. The function of cap 82 is preserve the specimen in collection tube 12 after transfer from urine collection device 16 and provide a leak resistant sealing during transport of the specimen to the laboratory for analysis.

Cap 82 has a piercing member 84 off centered and protruding from cap 82. Piercing member 84 is preferably a blunt cannula but may be a sharp-ended needle cannula. Piercing member 84 is in fluid communication with collection tube 12 such that when piercing member 84 pierces valve 40, the specimen flows through piercing member 84 and into collection tube 12. Cap 82 further includes a closure 90. Closure 90 may be hingedly attached to cap 82. Closure 90 also provides leak resistant protection from the specimen inside collection tube 12 when the closure is rotated and sealed over the cap. When the cap is sealed by the closure a permanent or tamper-resistant seal is formed between closure 90 and cap 82. Access to the specimen inside collection tube 12. at this point is only obtained by rotation or removal of cap 82.

As shown in FIG. 6, closure 90 has a retaining plug 100 centered and protruding from closure 90. The function of retaining plug 100 is to provide secure and releasable locking engagement of collection tube 12 to base 14 and urine collection device 16. When closure 90 is rotated over to seal cap 82, retaining plug 100 does not interact with any component of cap 82. The permanent seal formed between closure 90 and cap 82 and piercing member 84 does not involve retaining plug 100 but only closure 90. Piercing member 84 is off-centered and retaining plug 100 is off-centered such that there is clearance between both components.

Figure 5:
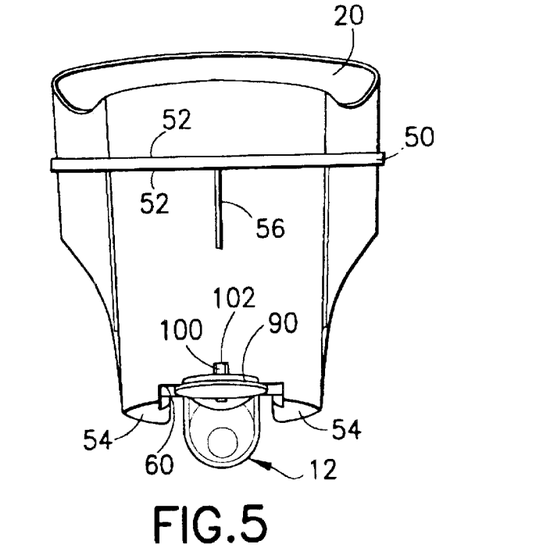
FIG. 5 illustrates a front view of the urine collection device of FIG. 1.

During sample collection, retaining plug 100 is inserted into retaining depression 102 for releasable and secure locking of collection tube 12 to base 14 and device 16 as shown in FIG. 5. Preferably, retaining plug 100 and retaining depression 102 are mating and releasable snap fits. Closure 90 releasably snaps into locking platform 60 to provide additional releasable and secure locking to collection tube 12. Retaining plug 100 with mating component retaining depression 102 and closure 90 with mating component locking platform 60 provide releasable locking and safety of collection tube 12 during the transfer of the specimen. Locking platform 60 also has a mating and releasable snap fit design in combination with the edges of closure 90. It is well known to those skilled in the art the various snap fit designs retaining plug 100 has with retaining depression 102 and closure 90 has with locking platform 60. Such snap fit designs include cantilever snaps, annular snap joints, and discontinuous annular snap joints.

Insertion of piercing member 84 into valve 40 also provides some support for collection tube 12. Alignment of the cap so that the piercing member extends into the valve is done without any difficult manipulation. As shown in FIG. 6, cap 82 slides over valve 40. Alignment of the piercing member is achieved during insertion by sliding the cap over the valve such that the inside of the cap comes in contact with the valve. Removal of collection tube 12 from device 16 after use is accomplished by depressing closure 90 in a downward direction to disengage retaining plug 100 from retaining depression 102 and closure 90 from locking platform 60. Piercing member 84 is then removed from valve 40. Prior to removal of the collection tube, the device is tilted by holding onto the finger placement platform in a direction parallel to the tube and away from valve 40 to assure the specimen will not flow toward the valve. The incline of top area 94 stops the flow of specimen in this position.

Materials for the components of urine collection device 16 and assembly 10 are selected from the following groups of materials. Preferably, valve 40 is made of an elastomeric material. Such an elastomeric material includes, but is not limited to, ethylene-propylene-diene-monomer, styrene-butadiene block co-polymers, polyisoprene, polyisobutylene, silicone based rubber, polyester based polyurethane and polybutadiene elastomers. Urine collection device 16 is preferably a unitary structure, excluding attached valve 40, and is made of a thermoplastic material. Such thermoplastic material includes, but is not limited to, polyethylene, polypropylene, high impact polystyrene and acrylonitrile-butadiene-styrene terpolymer. Collection tube 12 may be made of glass, but is preferably made of a similar thermoplastic material to resist breakage. Cap 82 is preferably made of a similar thermoplastic material as previously listed. Lid 62 can be made of woven polyethylene, paper, or any thermoplastic material. Preferably, lid 62 is made of a material that is permeable to sterilization methods like ethylene oxide gas or gamma and e-beam radiation.

Operation of assembly 10 begins with removing lid 62 and taking the tube out of the device by releasing the tube from the snap-fit arms. Use of the assembly begins with holding finger placement platform 50 and collecting the specimen inside device 16 through open top 20. Collection can occur with or without collection tube 12 attached because valve 40 is a closed valve. Valve 40 does not open until pierced by piercing member 84 on cap 82. Thus, no leakage or spills of the specimen occurs if collection tube 12 is not attached to device 16 prior to collection. After the specimen is collected, if collection tube 12 is not attached, it is attached either by the user or medical technician. Preferably, this operation of attachment is done by the medical technician to provide control over the transfer process and minimize the risk of contamination of the specimen from user tampering. Piercing member 84 on cap 82 punctures valve 40 so that collection tube 12 is in fluid communication with urine collection device 16. Piercing member 84 is preferably a blunt cannula to reduce the risk of injury. When piercing member 84 has entered valve 40, collection tube 12 is positioned and attached to device 16 at an oblique angle to arcuate base 14 for filling collection tube 12 to a predetermined volume when the device is held level or placed on a flat surface. Altering the angle of tube 12 relative to plane "A" can vary this predetermined volume. Once the required volume of specimen is transferred the device is tilted by holding the finger placement platform and tilting the device in the direction away from valve 40 and parallel to the tube. The incline of top area 94 stops the flow of the specimen towards the valve. The tube is then removed. Once piercing member 84 is removed, valve 40 self-seals and prevents further transfer of the specimen out of device 16. The device can be positioned back on a flat surface. Closure 90 is then rotated over cap 82 to form a permanent seal. Collection tube 12 is now ready for shipment to a laboratory for analysis. Another tube can be attached to device 16 if additional specimen samples are desired.

The embodiment depicted in FIGS. 1–7 is intended to be merely exemplary, and is not intended to depict all possible shapes for a collection device of the present invention. Rather, collection tube 12 and integrated valve 40 can be used with any shaped collection device that has mating components such as locking platform 60 and retaining depression 102 locking platform 60 and retaining depression 102 provide releasable locking and safety during the transfer of the specimen.

The present invention allows control over the volume of specimen transferred into collection tube 12 by the angle and position of valve 40 when the device is held or placed at a level orientation. In addition, collection tube 12 is securely and releasably attached during sample collection to urine collection device 16. Thus, the present invention enables the specimen to be transferred at various volumes while providing safety from spills or leakage by controlling the angle device 16 holds collection tube 12.

What is claimed is:

1. A method for collecting and transferring a urine specimen comprising the steps of:

holding a urine collection device having an arcuate base, an open top defining a plane, and a side wall extending from said base to said open top, said base having an inclined top surface, a bottom surface and a conduit passing through said top surface and said bottom surface, said device further Including a valve angularly attached and recessed in said base such that said valve is in fluid communication with said conduit and said base, said device further having a finger placement platform horizontally mounted on said side wall and having a gripping surface such that said gripping surface is perpendicularly and horizontally oriented from said side wall, said urine collection device being held by said finger placement platform;

collecting the specimen in said urine collection device;

attaching a collection tube having a blunt cannula to puncture said valve such that said tube is positioned and attached at an oblique angle to said base relative to said plane for filling said collection tube to a predetermined volume, when said device is placed on a level surface, transferring the specimen into said collection tube at a predetermined volume;

tilting said device in a direction parallel to said tube and away from said valve so that said inclined top area stops the specimen flow toward said valve; and removing said collection tube from said device.

2. A method for collecting and transferring a urine specimen, comprising the steps of:

holding a urine collection device assembly having an arcuate base, an open top defining a plane, and a side wall extending from said base to said open top, said base having an inclined top surface, a bottom surface and a conduit passing through said top surface and said bottom surface, said device further including a valve angularly attached and recessed in said base such that said valve is in fluid communication with said conduit and said base, said device further having a finger placement platform horizontally mounted on said side wall and having a gripping surface such that said gripping surface is perpendicularly and horizontally oriented from said side wall, and said device further having a collection tube having a blunt cannula for puncturing said valve such that said tube positioned and attached at an oblique angle to said base relative to said plane for filling said collection tube to a predetermined volume;

grasping said urine collection device assembly by said finger placement platform, collecting the specimen in said urine collection device assembly and simultaneously transferring the specimen into said tube when said device is place on a level surface;

tilting said device in a direction parallel to said tube and away from said valve so that said inclined top area stops the specimen flow toward said valve; and removing said collection tube from said valve.

3. A urine collection device assembly comprising:

an accurate base, an open top defining a plane, and sidewalls extending from said base to said open top, said base having an inclined top surface, a bottom surface, a conduit passing therethrough, wherein said arcuate base further includes a planar portion located adjacent to an integrate valve for providing flat surface support having a locking platform for securely and releasably locking a closure of a collection tube to said base during sample collection comprising a retaining depression for receiving a retaining plug such that insertions of said plug into said depression during sample collection provides for secure and releasable locking of the collection tube to said base; and said valve in fluid communication with said conduit and said base, said valve angularly attached to said base such that when the collection tube is attached to said valve, the collection tube is obliquely positioned with respect to said plane for filling the tube to a predetermined volume; and a tube holder fin centrally located on said bottom surface for holding the collection tube during collection; and releasable snap fit arms disposed on said top surface for holding the collection tube during storage of the device; and a top area inclined in the opposite direction of said top surface and adjacent to said top surface for resisting the flow of the fluid toward said valve when the collection tube is removed.

4. The urine collection device of claim 3 further comprising a finger placement platform having a gripping surface for holding the device, said platform mounted to said side wall such that said gripping surface is perpendicularly and horizontally oriented from said side wall.

5. The urine collection device of claim 3 wherein said valve is recessed within said base.

6. A urine collection device assembly comprising:

an accurate base, an open defining a plane, and sidewalls extending from said base to said open top, said base having an inclined top surface, a top area, a bottom surface, a conduit passing therethrough, said top surface inclined with respect to said plane and inclined in the opposite direction of said top area, wherein said arcuate base further includes a planar portion located adjacent to an integrate valve for providing flat surface support having a locking platform for securely and releasably locking a closure of a collection tube to said base during sample collection and said locking platform further includes a retaining depression and said closure further includes a retaining plug, such that insertion of said plug into said depression during sample collection provides for secure and releasable locking of the collection tube to said base; and said valve in fluid communication with said conduit and said base, said valve recessed within said base and angularly attached to said arcuate base such that when said collection tube is attached to said valve, the collection tube is obliquely positioned with respect to said plane for filling the collection tube to a predetermined volume; and a collection tube having a top, a closed bottom, a cylindrical side wall extending from said closed bottom to said top, and a cap disposed on said top, comprising a piercing member offset from a center axis of said cap and in fluid communication with said collection tube for puncturing said valve and said closure connected to said cap such that when said closure is rotated on said cap a permanent and tamper-resistant seal among said closure and said cap and said piercing member is formed and access to the fluid in the collection tube is only through removal of said cap; and a tube holder fin centrally located on said bottom surface for holding the collection tube during collection; and snap fit arms disposed on said top surface for holding the collection tube during storage of the device; and a finger placement platform having a gripper surface for holding the assembly, said platform mounted to said side wall such that said gripping surface is perpendicularly and horizontally oriented from said oblong side wall; and and a lid adjacent to said open top.

* * * * *